US012121546B2

(12) United States Patent
Brown et al.

(10) Patent No.: US 12,121,546 B2
(45) Date of Patent: Oct. 22, 2024

(54) TREATMENT OF SYSTEMIC INFLAMMATORY RESPONSES

(71) Applicant: Noveome Biotherapeutics, Inc., Pittsburgh, PA (US)

(72) Inventors: Larry R. Brown, Newton, MA (US); Howard C. Wessel, Sarver, PA (US)

(73) Assignee: Noveome Biotherapeutics, Inc., Pittsburght, PA (US)

( * ) Notice: Subject to any disclaimer, the term of this patent is extended or adjusted under 35 U.S.C. 154(b) by 553 days.

(21) Appl. No.: 17/197,714

(22) Filed: Mar. 10, 2021

(65) Prior Publication Data

US 2021/0196762 A1 Jul. 1, 2021

Related U.S. Application Data

(60) Continuation of application No. 16/370,923, filed on Mar. 30, 2019, now abandoned, which is a continuation of application No. 15/990,718, filed on May 28, 2018, now abandoned, which is a division of application No. 15/492,446, filed on Apr. 20, 2017, now Pat. No. 9,980,987, which is a division of application No. 14/717,330, filed on May 20, 2015, now abandoned.

(60) Provisional application No. 62/001,378, filed on May 21, 2014.

(51) Int. Cl.
A61K 38/18 (2006.01)
A61K 35/50 (2015.01)
A61K 38/19 (2006.01)
A61K 38/57 (2006.01)

(52) U.S. Cl.
CPC .............. *A61K 35/50* (2013.01); *A61K 38/18* (2013.01); *A61K 38/1858* (2013.01); *A61K 38/1866* (2013.01); *A61K 38/1891* (2013.01); *A61K 38/19* (2013.01); *A61K 38/191* (2013.01); *A61K 38/57* (2013.01)

(58) Field of Classification Search
CPC .... A61K 35/50; A61K 38/18; A61K 38/1858; A61K 38/1866; A61K 38/1891; A61K 38/19; A61K 38/191; A61K 38/57
See application file for complete search history.

(56) References Cited

U.S. PATENT DOCUMENTS

| 8,088,732 | B2 | 1/2012 | Marshall et al. |
| 8,278,095 | B2 | 10/2012 | Clarke et al. |
| 8,741,646 | B2 | 6/2014 | Emig et al. |
| 9,980,987 | B2 | 5/2018 | Brown et al. |
| 2009/0004161 | A1* | 1/2009 | Palladino ............ A61P 17/10 424/520 |
| 2015/0335712 | A1 | 11/2015 | Brown et al. |
| 2018/0271916 | A1 | 9/2018 | Brown et al. |
| 2020/0261512 | A1 | 8/2020 | Brown et al. |

OTHER PUBLICATIONS

Acute Respiratory Distress Syndrome (ARDS), Merck manual, accessed Jul. 28, 2023 at URL merckmanuals.com/home/lung-and-airway-disorders/respiratory-failure-and-acute-respiratory-distress-syndrome/ (Year: 2023).*
Antin et al., "Cytokine Dysregulation and Acute Graft-Versus-Host Disease," Blood 80:2964-2968 (1992) (Year: 1992).*
Tisoncik et al., "Into the eye of the cytokine storm," microbiology and molecular biology reviews 76: 16-32 (2012) (Year: 2012).*
U.S. Appl. No. 17/197,580, Noveome Biotherapeutics, Inc.
Major et al., Type I and III interferons disrupt lung epithelial repair during recovery from viral infection, Science 369, 712-717 (Aug. 2020).
McDermott et al., Conserved host response to highly pathogenic avian influenza virus infection in human cell culture, mouse and macaque model systems, BMC Systems Biology, 5(190):1-23 (2011) (http:///www.biomedcentral.com/1752-0509-5-190).
Rubenfeld et al., Incidence and Outcomes of Acute Lung Injury, N Engl. J Med, 353(16):685-1693 (Oct. 2005).
Steed et al., Amnion-derived Cellular Cytokine Solution: A Physiological Combination of Cytokines for Wound Healing, J Plastic Surgery, vol. 8, 157-165 (Apr. 2008).
Tisoncik et al., Into the Eye of the Cytokine Storm, Microbiology and Molecular Biology Review, 76(1):16-32 (Mar. 2012).
Marshall et al., A minimal common outcome measure set for COVID-19 clinical research, WHO Working Group on the Clinical Characterisation and Management of COVID-19 inection, Lancet Infect Dis, 20:e192-0197 (2020).
Zhou et al., Clinical course and risk factors for mortality of adult inpatients with COVID-19 in Wuhan, China: a retrospective cohort study, Lancet, 395:1054-1062 (Mar. 2020).
Aghagoli et al., Neurological Involvement in COVID-19 and Potential Mechanisms: A Review, Neurocrit Care, 10 pp. (Jul. 2020).
Channappanavar et al., Pathogenic human coronavirus infections: causes and consequences of cytokine storm and immunopathology, Semin Immunopathol, 39:529-539 (Apr. 2017).
Davidson et al., IFN is a potent anti-influenza therapeutic without the inflammatory side effects of IFN treatment, EMBO Molecular Medicine, 8(9):1099-1112 (2016).

(Continued)

*Primary Examiner* — Julie Ha
*Assistant Examiner* — Kristina M Hellman
(74) *Attorney, Agent, or Firm* — Dentons Cohen & Grigsby P.C.

(57) ABSTRACT

The invention is directed to methods for the treatment of diseases and conditions caused by increased vascular permeability. The invention is also directed to methods for returning vascular permeability that is a symptom of a disease or condition to a homeostatic state. Specifically, the invention is directed to methods for the treatment of diseases and conditions caused by increased vascular permeability or returning vascular permeability that is a symptom of a disease or condition to a homeostatic state by administering to a subject suffering from such diseases and conditions and symptoms novel cellular factor-containing solution compositions (referred to herein as "CFS" compositions), including novel sustained-release cellular factor-containing solution compositions (referred to herein as "SR-CFS" compositions).

7 Claims, No Drawings

(56) References Cited

OTHER PUBLICATIONS

Deng-Bryant, Treatment with amnion-derived cellular cytokine solution (ACCS) induces persistent motor improvement and ameliorates neuroinflammation in a rat model of penetrating ballistic-like brain injury, Restorative Neurology and Neuroscience 33, 189-203 (2015).

Borrega et al., In the Eye of the Storm: Immune-mediated Toxicities Associated with CAR-T Cell Therapy, HemaSphere, 3(2):e191-211 (2019).

Grinblat et al., RGC Neuroprotection Following Optic Nerve Trauma Mediated by Intranasal Delivery of Amnion Cell Secretome, Investigating Ophthalmology & Visual Science, 59(6):2470-2477 (May 2018).

Guan et al., Topical application of ST266 reduces UV-induced skin damage, Clinical, Cosmetic and Investigational Dermatology, vol. 10, 459-471 (2017).

Huong et al., Clinical features of patients infected with 2019 novel coronavirus in Wuhan, China, Lancet, vol. 395, 497-506 (Jan. 2020).

Jin et al., Endothelial activation and dysfunction in COVID-19: from basic mechanisms to potential therapeutic approaches, Nature, Signal Transduction and Targeted Therapy, 5(293):1-13 (Nov. 2020).

Khan et al., Intranasal Delivery of a Novel Amnion Cell Secretome Prevents Neuronal Damage and Preserves Function in a Mouse Multiple Sclerosis Model, Scientific Reports, 7(41768):1-12 (Dec. 2016).

Khan et al., Effects of Varying Intranasal Treatment Regimens in ST266-Mediated Retinal Ganglion Cell Neuroprotection, Journal of Neuro-Ophthalmology Basic and Translational Research, 00:1-9 (2019).

Leng et al., Transplantation of ACE2 Mesenchymal Stem Cells Improves the Outcome of Patients with COVID-19 Pneumonia, Aging and Disease, 11(2):216-228 (Apr. 2020).

Lowenstein et al., Severe COVID-19 is a Microvascular Disease, Circulation, 142:1609-1611(Oct. 2020).

* cited by examiner

TREATMENT OF SYSTEMIC INFLAMMATORY RESPONSES

FIELD OF THE INVENTION

The field of the invention is directed to methods for the treatment of diseases and conditions caused by increased vascular permeability. The field of the invention is also directed to methods for returning vascular permeability that is a symptom of a disease or condition to a homeostatic state. Specifically, the field of the invention is directed to methods for the treatment of diseases and conditions caused by increased vascular permeability or returning vascular permeability that is a symptom of a disease or condition to a homeostatic state by administering to a subject suffering from such diseases and conditions and symptoms novel cellular factor-containing solution compositions (referred to herein as "CFS" compositions), including novel sustained-release cellular factor-containing solution compositions (referred to herein as "SR-CFS" compositions).

BACKGROUND OF THE INVENTION

Vascular permeability, often in the form of capillary permeability or microvascular permeability, characterizes the capacity of a blood vessel wall to allow for the flow of small molecules (i.e., ions, water, nutrients), large molecules (i.e., albumin, antibodies, cytokines, nucleic acids, lipids) or even whole cells (i.e., lymphocytes on their way to a site of inflammation) in and out of the blood vessel. A single layer of endothelial cells, called endothelium, line the blood vessel walls and the heart chambers. Gaps which are located between the endothelial cells (called cell junctions) are able to open or close, but are strictly regulated depending on the type and physiological state of the tissue.

There are many triggers for vascular permeability. For example, an increase in vascular permeability occurs at the very beginning of the inflammatory response and is initially triggered by agents released by mast cells, which activate endothelial cell receptors promoting endothelial cell retraction and gap junction disorganization, leading to gap formation between the endothelial cells in venules and capillaries. (Garcia Leme, J., Hamamura, L., Leite, M. P., Rocha e Silva, M., 1973. Pharmacological analysis of the acute inflammatory process induced in the rat's paw by local injection of carrageenan and by heating. Br. J. Pharmacol. 48, 88-96.; Holsapple, M. P., Schnur, M., Yim, G. K., 1980. Pharmacological modulation of edema mediated by prostaglandin, serotonin and histamine. Agents Actions 10, 368-373.) The subsequent leakage of macromolecules to the injured tissue is the main cause of edema formation. A neutrophil-endothelium interaction, which is necessary for neutrophil migration, will then contribute to a more persistent increase in vascular permeability (Kubes, P., Gaboury, J. P., 1996. Rapid mast cell activation causes leukocyte-dependent and -independent permeability alterations. Am. J. Physiol. 271, H2438-H2446.; Lewis, R. E., Granger, H. J., 1986. Neutrophil-dependent mediation of microvascular permeability. Fed. Proc. 45, 109-113).

In acute inflammation, fluid loss from blood vessels with increased permeability occurs in distinct phases: (1) an immediate transient response lasting for 30 minutes or less, mediated mainly by the actions of histamine and leukotrienes on endothelium; (2) a delayed response starting at about 2 hours and lasting for about 8 hours, mediated by kinins, complement products, and other factors; and (3) a prolonged response that is most noticeable after direct endothelial injury, for example, after burns.

A critical function of inflammation is to deliver leukocytes to the site of injury and to activate the leukocytes to perform their normal functions in host defense. Leukocytes ingest offending agents, kill bacteria and other microbes, and get rid of necrotic tissue and foreign substances. However, untoward events manifest themselves as a result of the defensive potency of leukocytes. For example, leukocytes may induce tissue damage and prolong inflammation and leukocyte products that destroy microbes and necrotic tissues can also injure normal host tissues.

Increased vascular permeability is also exhibited by certain viral diseases called viral hemorrhagic fevers (VHFs). VHF refers to a group of illnesses that are caused by several distinct families of viruses. In general, the term "viral hemorrhagic fever" is used to describe a severe multisystem syndrome in which the overall vascular system is damaged, and the body's ability to regulate itself is impaired. These symptoms are often accompanied by hemorrhage; however, the bleeding itself is rarely life-threatening. While some types of VHFs can cause relatively mild illnesses, many of these viruses cause severe, life-threatening disease. Examples include Ebola, Marburg, Lassa fever, and yellow fever viruses, among others.

Currently, there is no universal, satisfactory treatment for many of the VHFs, particularly those that cause life-threatening disease. Treatments include transfusion of serum from patients that have recovered from the viral infection as well as aggressive treatment of symptoms including nausea, vomiting, diarrhea, fever, and bleeding.

It is believed that a treatment option that could reduce abnormal vascular permeability associated with certain diseases and conditions or which is a symptom of certain diseases and conditions would vastly benefit patients who otherwise have few treatment options. In particular, a treatment option that could decrease vascular permeability could prove very useful in the management of the notoriously difficult VHF diseases.

Accordingly, it is an object of the instant invention to provide such a treatment options.

BRIEF SUMMARY OF THE INVENTION

The instant invention provides novel cellular factor-containing solution (CFS) compositions, including Amnion-derived Cellular Cytokine Solution (ACCS) (see U.S. Pat. Nos. 8,058,066 and 8,088,732, both of which are incorporated herein by reference), for use in the described methods for the treatment of diseases and conditions caused by increased vascular permeability or returning vascular permeability that is a symptom of a disease or condition to a homeostatic state, such as VHFs. Applicant has discovered that ACCS, which contains more than 200 proteins, cytokines, and growth factors, universally modulates vascular permeability. Applicant has discovered that ACCS modulates vascular permeability in human umbilical vein endothelial cells (HUVECs) in tissue culture. Based on these discoveries, Applicant has further discovered that in vivo, ACCS will result in the modulation of vascular permeability as assessed using the Miles Assay (see A. A. Miles and E. M. Miles, Vascular reactions to histamine, histamine-liberator and leukotaxine in the skin of guinea-pigs, J. Physiol. (1952) 118, 228-257), the contents of which is incorporated herein by reference in its entirety. Applicant has shown that ACCS decreases vascular permeability stimulated by several different stimulators including VEGF (an angiogenic protein factor), histamine (an organic nitrogenous compound involved in local immune responses), bradykinin (a peptide that causes blood vessels to dilate) and TNFα (a cell signaling protein (cytokine) involved in systemic inflammation), thus demonstrating that ACCS may be used as a universal agent to treat many diseases or conditions that are characterized by increases in vascular permeability as well as vascular permeability that is a symptom of a disease or condition. By way of non-limiting example, insults resulting from burns, physical injuries, infections, wounds, radiation exposure, pulmonary edema, periodontal disease, pulmonary fibrosis, acute respiratory distress syndrome, severe pustular psoriasis, septic shock, hyperpermeability triggered by inflammation or ischemia in the heart, brain, or lung that promotes edema and exacerbates disease progression and impairs recovery, insect bites, natural or synthetic chemical irritants, frostbite, toxins, infection by pathogens (for example, viruses that cause VHFs), immune reactions due to hypersensitivity, foreign bodies including splinters, dirt and debris, stress, trauma, alcohol, appendicitis, bursitis, colitis, cystitis, dermatitis, phlebitis, rhinitis, tendonitis, tonsillitis, vasculitis, release of prostaglandins (E1, E2, F1α and F2α), histamine, serotonin, bradykinin, lipopolysaccharides, cytokines or growth factors such as VEGF, interleukins, TNF-α, etc. resulting in increased vascular permeability and deviation from homeostatic vascular permeability could benefit from the methods of the invention.

Other diseases, disorders and conditions characterized by undesirable vascular permeability include, for example, edema, Meigs' syndrome, lung inflammation, nephrotic syndrome, pericardial effusion, pleural effusion, acute lung injury, inflammatory bowel disease, ischemia/reperfusion injury in stroke, myocardial infarction, and infectious and non-infectious diseases that result in a cytokine storm. Though a cytokine storm is the systemic expression of a healthy and vigorous immune system, it is an exaggerated immune response caused by rapidly proliferating and highly activated T-cells or natural killer (NK) cells and results in the release of more than 150 inflammatory mediators (including cytokines, oxygen free radicals, and coagulation factors). Both pro-inflammatory cytokines (i.e., TNF-α, IFN-γ, IL-1β, IL-2, IL-15 and IL-6) and anti-inflammatory cytokines (i.e., IL-10, and IL-1ra) are elevated in the serum, and it is the fierce and often lethal interplay of these cytokines that characterizes the "cytokine storm."

Cytokine storms can occur in a number of infectious and non-infectious diseases including, for example, graft-versus-host disease (GVHD), adult respiratory distress syndrome (ARDS), sepsis, avian influenza, smallpox, and systemic inflammatory response syndrome (SIRS). In the absence of prompt intervention, a cytokine storm can result in permanent lung damage and, in many cases, death. Many patients will develop ARDS, which is characterized by pulmonary edema that is not associated with volume overload or depressed left ventricular function. The end stage symptoms of a disease precipitating the cytokine storm may include one or more of the following: hypotension, tachycardia, dyspnea, fever, ischemia or insufficient tissue perfusion, uncontrollable hemorrhage, severe metabolism dysregulation, and multisystem organ failure. Deaths from infections that precipitate a cytokine storm are often attributable to the symptoms resulting from the cytokine storm and are, therefore, not directly caused by the relevant pathogen. For example, death in severe influenza infections, such as avian influenza or "bird flu," is typically the result of ARDS, which results from a cytokine storm triggered by the viral infection.

Accordingly, a first aspect of the invention is a method for treating diseases and conditions caused by increased vascular permeability in a patient in need thereof comprising administering to the patient a therapeutically effective amount of a CFS composition.

A second aspect of the invention is method for returning vascular permeability that is a symptom of a disease or condition to homeostatic state in a patient in need thereof comprising administering to the patient a therapeutically effective amount of a CFS composition.

A third aspect of the invention is a method for treating viral hemorrhagic fever in a patient in need thereof comprising administering to the patient a therapeutically effective amount of a CFS composition.

Specific embodiments of aspects 1, 2 and 3 of the invention are ones in which the CFS composition is ACCS; the CFS composition, including ACCS, is formulated for topical or intranasal administration; the CFS composition, including ACCS, is formulated for parenteral administration; the CFS composition, including ACCS, is formulated for enteral administration.

In still other embodiments of the invention, the diseases and conditions caused by increased vascular permeability or exhibited vascular permeability as a symptom are selected from the group consisting of burns, physical injuries, infections, wounds, radiation exposure, pulmonary edema, periodontal disease, pulmonary fibrosis, acute respiratory distress syndrome, septic shock, hyperpermeability triggered by inflammation or ischemia in the heart, brain, or lung, insect bites, natural or synthetic chemical irritants, frostbite, toxins, infection by pathogens, immune reactions due to hypersensitivity, foreign bodies, stress, trauma, alcohol, appendicitis, bursitis, colitis, cystitis, dermatitis, phlebitis, rhinitis, tendonitis, tonsillitis, vasculitis, release of prostaglandins (E1, E2, F1α and F2α), histamine, serotonin, bradykinin, cytokine storms, and lipopolysaccharides.

Definitions

As defined herein "isolated" refers to material removed from its original environment and is thus altered "by the hand of man" from its natural state.

As used herein, the term "protein marker" means any protein molecule characteristic of the plasma membrane of a cell or in some cases of a specific cell type.

As used herein, "enriched" means to selectively concentrate or to increase the amount of one or more materials by elimination of the unwanted materials or selection and separation of desirable materials from a mixture (i.e., separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning. In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning. Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "extraembryonic tissue" means tissue located outside the embryonic body which is involved with the embryo's protection, nutrition, waste removal, etc. Extraembryonic tissue is discarded at birth. Extraembryonic tissue includes but is not limited to the amnion, chorion (trophoblast and extraembryonic mesoderm including umbilical cord and vessels), yolk sac, allantois and amniotic fluid (including all components contained therein). Extraembryonic tissue and cells derived therefrom have the same genotype as the developing embryo.

As used herein, the term "extraembryonic cytokine secreting cells" or "ECS cells" means a population of cells derived from the extraembryonic tissue which have the characteristics of secreting a unique combination of physiologically relevant cytokines in a physiologically relevant temporal manner into the extracellular space or into surrounding culture media and which have not been cultured in the presence of any non-human animal-derived products, making them and cell products derived from them suitable for human clinical use. In a preferred embodiment, the ECS cells secrete the cytokines VEGF, Angiogenin, PDGF and the MMP inhibitors TIMP-1 and/or TIMP-2. The physiological range of the cytokine or cytokines in the unique combination is as follows: ~5-16 ng/mL for VEGF, ~3.5-4.5 ng/ml for Angiogenin, ~100-165 pg/mL for PDGF, ~0.68 μg/mL for TIMP-1 and ~1.04 μg/mL for TIMP-2.

As used herein, the term "amnion-derived multipotent progenitor cell" or "AMP cell" means a specific population of ECS cells that are epithelial cells derived from the amnion. In addition to the characteristics described above for ECS cells, AMP cells have the following characteristics. They have not been cultured in the presence of any non-human animal-derived products, making them and cell products derived from them suitable for human clinical use. They grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated amnion epithelial cells, from which AMP cells are selected, will have no reaction with an antibody to the stem/progenitor cell marker c-kit (CD117), and minimal to no reaction with an antibody to the stem/progenitor cell marker Thy-1 (CD90). Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172:493-500). However, the methods described herein provide improved, novel compositions and populations of cells.

By the term "animal-free" when referring to certain compositions, growth conditions, culture media, etc. described herein, is meant that no non-human animal-derived materials, such as bovine serum, proteins, lipids, carbohydrates, nucleic acids, vitamins, etc., are used in the preparation, growth, culturing, expansion, storage or formulation of the cell, composition or process. By "no non-human animal-derived materials" is meant that the materials have never been in or in contact with a non-human animal body or substance so they are not xeno-contaminated. Only clinical grade materials, such as recombinantly produced human proteins, are used in the preparation, growth, culturing, expansion, storage and/or formulation of such cells, compositions and/or processes.

By the term "serum-free" when referring to certain compositions, growth conditions, culture media, etc., described herein, is meant that no animal-derived serum (i.e., no non-human) is used in the preparation, growth, culturing, expansion, storage or formulation of the cells, composition or process.

By the term "expanded", in reference to cell compositions, means that the cell population constitutes a significantly higher concentration of cells than is obtained using previous methods. For example, the level of cells per gram of amniotic tissue in expanded compositions of AMP cells is at least 50 and up to 150 fold higher than the number of cells in the primary culture after 5 passages, as compared to about a 20-fold increase in such cells using previous methods. In another example, the level of cells per gram of amniotic tissue in expanded compositions of AMP cells is at least 30 and up to 100 fold higher than the number of cells in the primary culture after 3 passages. Accordingly, an "expanded" population has at least a 2 fold, and up to a 10 fold, improvement in cell numbers per gram of amniotic tissue over previous methods. The term "expanded" is meant to cover only those situations in which a person has intervened to elevate the number of the cells.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, chemokines, receptors, inhibitors and granules. The medium containing the cellular factors is the conditioned medium.

As used herein, the term "cellular factor-containing solution" or "CFS" composition means a composition having physiologic concentrations of one or more protein factors. CFS compositions include conditioned media derived from ECS cells, amnion-derived cellular cytokine solution compositions (see definition below), physiologic cytokine solution compositions (see definition below), and sustained release formulations of such CFS compositions.

As used herein, the term "amnion-derived cellular cytokine solution" or "ACCS" means conditioned medium that has been derived from AMP cells or expanded AMP cells.

As used herein, the term "physiologic cytokine solution" or "PCS" composition means a composition which is not cell-derived and which has physiologic concentrations of VEGF, Angiogenin, PDGF and TGFβ2, TIMP-1 and TIMP-2.

As used herein, the term "suspension" means a liquid containing dispersed components, i.e., cytokines. The dispersed components may be fully solubilized, partially solubilized, suspended or otherwise dispersed in the liquid. Suitable liquids include, but are not limited to, water, osmotic solutions such as salt and/or sugar solutions, cell culture media, and other aqueous or non-aqueous solutions.

The term "lysate" as used herein refers to the composition obtained when cells, for example, AMP cells, are lysed and optionally the cellular debris (e.g., cellular membranes) is removed. This may be achieved by mechanical means, by freezing and thawing, by sonication, by use of detergents, such as EDTA, or by enzymatic digestion using, for example, hyaluronidase, dispase, proteases, and nucleases. In some instances, it may be desirable to retain the cellular debris (e.g., cellular membranes) as well.

The term "physiologic" or "physiological level" as used herein means the level that a substance in a living system is found and that is relevant to the proper functioning of a biochemical and/or biological process.

As used herein, the term "substrate" means a defined coating on a surface that cells attach to, grow on, and/or migrate on. As used herein, the term "matrix" or "scaffold" means a three-dimensional (3D) structure that cells grow within or on that may or may not be defined in its components. It may be composed of biological components, synthetic components, or a combination of both. Further, it may be naturally constructed by cells (i.e., extracellular matrix) or artificially constructed. In addition, the matrix or scaffold may contain components that have biological activity under appropriate conditions.

The term "cell product" or "cell products" as used herein refers to any and all substances made by and secreted from a cell, including but not limited to, protein factors (i.e., growth factors, differentiation factors, engraftment factors, cytokines, morphogens, proteases (i.e., to promote endogenous cell delamination, protease inhibitors), extracellular matrix components (i.e., fibronectin, etc.).

The term "therapeutically effective amount" means that amount of a therapeutic agent necessary to achieve a desired physiological effect (i.e., treating diseases and conditions caused by increased vascular permeability or treating vascular permeability that is a symptom of a disease or condition).

As used herein, the term "pharmaceutically acceptable" means that the components, in addition to the therapeutic agent, comprising the formulation, are suitable for administration to the patient being treated in accordance with the present invention.

As used herein, the term "therapeutic component" means a component of the composition which exerts a therapeutic benefit when the composition is administered to a subject.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

As used herein, the term "tissue" refers to an aggregation of similarly specialized cells united in the performance of a particular function.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents.

As used herein, the term "agent" means an active agent or an inactive agent. By the term "active agent" is meant an agent that is capable of having a physiological effect when administered to a subject. Non-limiting examples of active agents include growth factors, cytokines, antibiotics, cells, conditioned media from cells, etc. By the term "inactive agent" is meant an agent that does not have a physiological effect when administered. Such agents may alternatively be called "pharmaceutically acceptable excipients". Non-limiting examples include time release capsules and the like.

The terms "parenteral administration" and "administered parenterally" are art-recognized and refer to modes of administration other than intranasal, enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, epidural, intracerebral, intraocular, subdural and intrasternal injection or infusion.

As used herein, the term "enteral" administration means any route of drug administration that involves absorption of the drug through the gastrointestinal tract. Enteral administration may be divided into three different categories: oral, gastric, and rectal.

As used herein, the term "topical" administration means a medication that is applied to body surfaces such as the skin or mucous membranes to treat ailments via a large range of classes including but not limited to liquids, sprays, creams, foams, gels, lotions, salves and ointments.

The term "intranasal" or "intranasal delivery" or "intranasal administration" as used herein means delivery within or administered by way of the nasal structures.

As used herein, the term "aerosol" means a cloud of solid or liquid particles in a gas.

The terms "particles", "aerosolized particles", and "aerosolized particles of formulation" are used interchangeably herein and shall mean particles of formulation comprised of any pharmaceutically active ingredient, preferably in combination with a carrier, (e.g., a pharmaceutically active respiratory drug and carrier). The particles have a size which is sufficiently small such that when the particles are formed they remain suspended in the air or gas for a sufficient amount of time such that a patient can inhale the particles into the patient's lungs. As used herein, the term "nebulizer" means a device used to reduce a liquid medication to extremely fine cloudlike particles (i.e. an aerosol). A nebulizer is useful in delivering medication to deeper parts of the respiratory tract. Nebulizers may also be referred to as atomizers and vaporizers.

The terms "sustained-release", "extended-release", "time-release", "controlled-release", or "continuous-release" as used herein means an agent, typically a therapeutic agent or drug, that is formulated to dissolve slowly and be released over time.

As used herein, the term "vascular permeability" means the capacity of a blood vessel wall to allow for the flow of small molecules (such as ions, water, and nutrients), large molecules (such as albumin, antibodies, cytokines, nucleic acids, and lipids), or even whole cells (such as lymphocytes, B cells, neutrophils, mast cells, macrophages, monocytes, eosinophils, and basophils) in to and out of the blood vessel.

The term "viral hemorrhagic fever" or "VHF" means any number of viral diseases including without limitation Ebola, Marburg, Lassa fever, and yellow fever viruses, among others.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

As used herein, a "wound" is any disruption, from whatever cause, of normal anatomy (internal and/or external anatomy) including but not limited to traumatic injuries such as mechanical (i.e. contusion, penetrating), thermal, chemical, electrical, radiation, concussive and incisional injuries; elective injuries such as operative surgery and resultant incisional hernias, fistulas, etc.; acute wounds, chronic wounds, infected wounds, and sterile wounds, as well as wounds associated with disease states (i.e., ulcers caused by diabetic neuropathy or ulcers of the gastrointestinal or genitourinary tract). A wound is dynamic and the process of healing is a continuum requiring a series of integrated and interrelated cellular processes that begin at the time of wounding and proceed beyond initial wound closure through arrival at a stable scar. These cellular processes are mediated or modulated by humoral substances including but not limited to cytokines, lymphokines, growth factors, and hormones. In accordance with the subject invention, "wound healing" refers to improving, by some form of intervention, the natural cellular processes and humoral substances of tissue repair such that healing is faster, and/or the resulting healed area has less scaring and/or the wounded area possesses tissue strength that is closer to that of uninjured tissue and/or the wounded tissue attains some degree of functional recovery.

As used herein the term "standard animal model" refers to any art-accepted animal model in which the compositions of the invention exhibit efficacy.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Exemplary Therapeutic Applications

Any insult resulting in increased vascular permeability could benefit from the methods of the invention. For example, in septic shock, the rate of loss of albumin to the tissue spaces rises by more than 300%. In cardiac surgery, it rises by 100% within 7 hours of the surgery. The transcapillary escape rate in cachectic cancer patients is twice that of a group of healthy individuals. Large rate increases in vascular permeability is often seen in acute and chronic disease.

Increased vascular permeability contributes to many diseases, including acute respiratory distress syndrome (ARDS), and inflammation. Most studies on the vascular barrier function have focused on soluble regulators, such as tumor-necrosis factor-$\alpha$ (TNF-$\alpha$). It has been shown that lung vascular permeability is controlled mechanically by changes in extracellular matrix structure. Studies reveal that pulmonary vascular leakage can be increased by altering extracellular matrix compliance in vitro and by manipulating lysyl oxidase-mediated collagen crosslinking in vivo. Either decreasing or increasing extracellular matrix stiffness relative to normal levels disrupts junctional integrity between endothelial cells and thus increases vascular leakage. (Akiko Mammoto, Tadanori Mammoto, Mathumai Kanapathipillai, Chong Wing Yung, Elisabeth Jiang, Amanda Jiang, Kristopher Lofgren, Elaine P. S. Gee, Donald E. Ingber, Control of lung vascular permeability and endotoxin-induced pulmonary oedema by changes in extracellular matrix mechanics, Nature Commun 4:1759. doi: 10.1038/ncomms2774, 2013).

Human pathologies such as vascular malformations, hemorrhagic stroke, and edema are associated with defects in the organization of endothelial cell junctions. Edema around the ischemic area extends brain damage in ischemic stroke. Inflammation is often associated with increases in vascular permeability, which favors leukocyte diapedesis through the vessel wall and may create pain and swelling. Edema is often reversible and the control of vascular permeability may be restored once the triggering cause is removed.

There are three microvascular events that characterize acute inflammation: arteriolar vasodilatation, neutrophil recruitment and vascular permeability increase. Applicant has previously demonstrated in various in vivo studies that ACCS decreases inflammation as seen by reduced neutrophil and leukocyte presence at the site of injury and that ACCS decreases inflammation in periodontitis (see U.S. Pat. No. 8,444,417, incorporated herein by reference in its entirety). The reduction of vascular permeability to more normal levels by ACCS would likely involve the interruption of pro-inflammatory cytokine cascades by its multitude of growth factor and cytokine components.

There are numerous cytokines, growth factors, and signal molecules which react with endothelial cell structural components which control vascular permeability. Interferon-gamma (IFN-γ), interleukin-1 alpha and beta (IL-1α and IL-1β) and tumor necrosis factor-alpha (TNF-α) have all been shown to increase endothelial monolayer permeability (Lal B K et al. (2001) VEGF increases permeability of the endothelial cell monolayer by activation of PKB/akt, endothelial nitric-oxide synthase, and MAP kinase pathways. Microvascular Research 62:252-262) VEGF increases permeability of the endothelial cell monolayer by activation of PKB/akt, endothelial nitric-oxide synthase, and MAP kinase pathways. Microvascular Research 62:252-262., Burke-Gaffney A et al. (1993) Modulation of human endothelial cell permeability by combinations of the cytokines interleukin-1 alpha/beta, tumor necrosis factor-alpha and interferon-gamma. Immunopharmacology 25:1-9., Marcus B C et al. (1996) Cytokine-induced increases in endothelial permeability occur after adhesion molecule expression. Surgery 120:411-417. Campbell W N et al. (1992) Interleukin-1 alpha and -beta augment pulmonary artery transendothelial albumin flux in vitro. American Journal of Physiology 263:128-136). Thrombin stimulation of cytoskeletal signaling pathways has been shown to manipulate cell permeability. Lipopolysaccharide (LPS) induces junction barrier loss and cell detachment by activating protein tyrosine kinases (PTKs) and caspase cleavage reactions (Bannerman D D et al. (1998) Bacterial lipopolysaccharide disrupts endothelial monolayer integrity and survival signaling events through caspase cleavage of adherens junction proteins. Journal of Biological Chemistry 273:35371-35380.). In contrast, junctional adhesion molecule (JAM) decreases permeability by initiating cell adhesion (Bazzoni G et al. (2000) Interaction of junctional adhesion molecule with the tight junction components ZO-1, cingulin, and occludin. Journal of Biological Chemistry 275:20520-20526) and angiopoietin-1 (Ang-1) protects endothelial barrier function through regulation of junctional molecules (Li X et al. (2008) Basal and angiopoietin-1-mediated endothelial permeability is regulated by sphingosine kinase-1. Blood 111:3489-3497, Gamble J R et al. (2000) Angiopoietin-1 is an anti-permeability and anti-inflammatory agent in vitro and targets cell junctions. Circulation Research 87:603-607).

Disruption of the endothelial barrier integrity is associated with many systemic disease states. Pathological angiogenic diseases include heart disease, diabetes, stroke, cancer, hypertension, arthritis, and Alzheimer's (Fu B M. (2001) Microvessel permeability and its regulation. Recent Advances in Biomechanics 231-247, Bates D O et al. (2002) Regulation of microvascular permeability by vascular endothelial growth factors. Journal of Anatomy 200:581-597, Mooradian A D. (1988) Effect of aging on the blood-brain barrier. Neurobiological Aging 9:31-39). In addition, increases in tissue permeability may be caused by any number of stimuli that affect tight junctions, gap junctions or matrix organizations.

One specific example of increased vascular permeability is in the initial lesion of periodontal disease, in which the gingival plexus becomes engorged and dilated, allowing large numbers of neutrophils to extravasate and appear within the junctional epithelium and underlying connective tissue (see Page, RC; Schroeder, HE. "Pathogenesis of Inflammatory Periodontal Disease: A Summary of Current Work." Lab Invest 1976; 34(3):235-249) (the contents of which is incorporated herein by reference in its entirety).

Increased vascular permeability is also exhibited by viral hemorrhagic fevers (VHFs). VHF refers to a group of illnesses that are caused by several distinct families of viruses. The term "viral hemorrhagic fever" is used to describe a severe multisystem syndrome in which the overall vascular system is damaged, and the body's ability to regulate itself is impaired. These symptoms are often accompanied by hemorrhage; however, the bleeding itself is rarely life-threatening. While some types of VHFs can cause relatively mild illnesses, many of these viruses cause severe, life-threatening disease. Examples include Ebola, Marburg, Lassa fever, and yellow fever viruses, among others.

Compositions and Methods of Making Compositions

Detailed information and methods on the preparation of AMP cell compositions, generation of ACCS, generation of pooled ACCS, detection of cytokines in non-pooled and pooled ACCS using ELISA, generation of PCS compositions, and generation of sustained-release CFS compositions can be found in U.S. Pat. Nos. 8,058,066, 8,088,732, 8,278, 095 all of which are incorporated herein by reference.

The invention provides for an article of manufacture comprising packaging material and a pharmaceutical composition of the invention contained within the packaging material, wherein the pharmaceutical composition comprises CFS compositions, including ACCS. The packaging material comprises a label or package insert which indicates that the CFS compositions, including ACCS, contained therein can be used for therapeutic applications such as, for example, treating diseases and conditions caused by increased vascular permeability or wherein vascular permeability is a symptom of a disease or condition.

Formulation, Dosage and Administration of CFS Compositions

Compositions comprising CFS compositions may be administered to a subject to provide various cellular or tissue functions, for example, treating diseases and conditions caused by increased vascular permeability. As used herein "subject" may mean either a human or non-human animal.

Such compositions may be formulated in any conventional manner using one or more physiologically acceptable carriers optionally comprising excipients and auxiliaries. Proper formulation is dependent upon the route of administration chosen. For topical administration, the CFS compositions may be formulated as a spray, liquid, cream, foam, gel, lotion, salve, and ointment, etc. The compositions may also be administered to the recipient in one or more physiologically acceptable carriers. Carriers for CFS compositions may include but are not limited to solutions of normal saline, phosphate buffered saline (PBS), lactated Ringer's solution containing a mixture of salts in physiologic concentrations, or cell culture medium.

For parenteral administration, the formulation may be injected intravenously.

For enteral administration, the formulation may be administered as an oral liquid, a capsule or tablet designed to release CFS compositions at a specific portion of the gastrointestinal tract.

For subcutaneous or intramuscular administration, the formulation may be delivered by needle and syringe, by pen injectors, by needleless injection devices and the like.

For intranasal administration, the formulation may be administered as a nasal spray, a nebulized pulmonary dosage form, a metered dose inhaler or a dry powder inhaler.

In addition, one of skill in the art may readily determine the appropriate dose of the CFS compositions for a particular purpose. An exemplary topical dose is in the range of about 0.1-to-10,000 milliliters per square centimeter of applied area. Other exemplary dose ranges are 1.0-to-1,000 milliliters/applied area. Exemplary intranasal and pulmonary delivery doses range from about 0.01 milliliters per dose to about 10,000 milliliters per dose. Exemplary oral doses range from about 0.01 milliliters to about 10,000 milliliters, or equivalent tableted dosage form. Exemplary injectable doses may range from about 0.01 milliliters to about 10,000 milliliters per administration. In a particular embodiment, it has been found that relatively small amounts of the CFS compositions are therapeutically useful. One exemplification of such therapeutic utility is the ability for ACCS (including pooled ACCS) to accelerate wound healing (for details see U.S. Publication No. 2006/0222634 and U.S. Pat. No. 8,187,881, both of which are incorporated herein by reference). One of skill in the art will also recognize that the number of doses to be administered needs also to be empirically determined based on, for example, severity and type of disease, disorder or injury being treated; patient age, weight, sex, health; other medications and treatments being administered to the patient; and the like. For example, in a specific embodiment, one dose is sufficient to have a therapeutic effect (i.e., treating diseases and conditions caused by increased vascular permeability or treating vascular permeability that is a symptom of a disease or condition). Other specific embodiments contemplate, 2, 3, 4, or more doses for therapeutic effect.

For VHFs, the administration is typically intravenous. The timing for administration needs to be empirically determined by the attending physician as each patient will develop symptoms at different time points following infection. Optimally, CFS will be administered as soon as symptoms first appear. This is necessary to prevent or minimize both the vascular permeability and the excessive release of cytokines, termed a cytokine storm, which could eventually causes death.

One of skill in the art will also recognize that number of doses (dosing regimen) to be administered needs also to be empirically determined based on, for example, severity and type of injury, disorder or condition being treated; patient age, weight, sex, health; other medications and treatments being administered to the patient; and the like. In addition, one of skill in the art recognizes that the frequency of dosing needs to be empirically determined based on similar criteria. In certain embodiments, one dose is administered every day for a given number of days (i.e., once a day for 7 days, etc.). In other embodiments, multiple doses may be administered in one day (every 4 hours, etc.). Multiple doses per day for multiple days are also contemplated by the invention.

In further embodiments of the present invention, at least one additional agent may be combined with the CFS compositions. Such agents may act synergistically with the CFS compositions of the invention to enhance the therapeutic effect. Such agents include but are not limited to growth factors, cytokines, chemokines, antibodies, inhibitors, antibiotics, immunosuppressive agents, steroids, anti-fungals, anti-virals or other cell types (i.e., stem cells or stem-like cells, for example, AMP cells). Inactive agents include carriers, diluents, stabilizers, gelling agents, delivery vehicles, ECMs (natural and synthetic), scaffolds, matrices and the like. When the CFS compositions are administered conjointly with other pharmaceutically active agents, even less of the CFS compositions may be needed to be therapeutically effective.

CFS compositions may also be inserted into a delivery device, e.g., a tube, in different forms. For example, the CFS compositions can be part of a solution contained in such a delivery device. As used herein, the term "solution" includes a pharmaceutically acceptable carrier or diluent. Pharmaceutically acceptable carriers and diluents include saline, aqueous buffer solutions, solvents and/or dispersion media. The use of such carriers and diluents is well known in the art. In certain applications it is be preferable for the solution to be fluid to the extent that easy syringe loading is possible. Preferably, the solution is stable under the conditions of manufacture and storage and may optionally be preserved against the contaminating action of microorganisms such as bacteria and fungi through the use of, for example, parabens, chlorobutanol, phenol, ascorbic acid, thimerosal, and the like. Solutions of the invention can be prepared by incorporating the CFS compositions in a pharmaceutically acceptable carrier or diluent and, as required, other ingredients enumerated above.

The timing of administration of CFS compositions will depend upon the type and severity of the disease, disorder, or injury being treated. In one embodiment, the CFS compositions are administered as soon as possible after onset of symptoms or diagnosis. In another embodiment, CFS compositions are administered more than one time following onset of symptoms or diagnosis.

Support matrices or scaffolds, including for example membranes and the like, into which the CFS compositions can be incorporated or embedded include substances which are recipient-compatible and which degrade into products which are not harmful to the recipient. Detailed information on suitable support matrices, etc. can be found in U.S. Pat. Nos. 8,058,066 and 8,088,732, both of which are incorporated herein by reference. Other suitable matrices and scaffolds are familiar in the art.

A "therapeutically effective amount" of a therapeutic agent within the meaning of the present invention will be determined by a patient's attending physician or veterinarian. Such amounts are readily ascertained by one of ordinary skill in the art and will enable treating diseases and conditions caused by increased vascular permeability when administered in accordance with the present invention. Factors which influence what a therapeutically effective amount will be include, the specific activity of the therapeutic agent being used, the extent of a wound, the absence or presence of infection, time elapsed since a surgery, and the age, physical condition, existence of other disease states, and nutritional status of the patient. Additionally, other medication the patient may be receiving will affect the determination of the therapeutically effective amount of the therapeutic agent to administer.

EXAMPLES

The following examples are put forth so as to provide those of ordinary skill in the art with a complete disclosure and description of how to make and use the compositions and methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Celsius, and pressure is at or near atmospheric.

Example 1: In Vitro Vascular Permeability Assays

Objective: TNF-α has been shown to increase endothelial monolayer permeability (Mark, K. S., et al., Life Sciences, 1999, 64(21): 1941-1953). In order to test whether ACCS has the ability to affect vascular permeability, initial experiments were performed to determine whether ACCS could reduce the level of permeability of endothelial cells exposed to TNF-α.

Method: The ability of ACCS to modulate vascular permeability was evaluated using an In Vitro Vascular Permeability Assay (Millipore, Cat. No. ECM640). In this assay, Human vascular endothelial cells (HUVEC) were seeded onto collagen or fibrin-coated semi-permeable membrane inserts and a monolayer of cells was formed which occluded the membrane pores. The inserts were then placed in a receiver well. The cell monolayer can be treated with cytokines, growth factors, or other compounds of interest. In this experiment, the cells were treated with TNF-α and a high molecular weight FITC-labeled Dextran added to the top of the cells. The FITC-Dextran molecules are able to pass through the endothelial cell monolayer into the receiver well solution at a rate proportional to the monolayer's permeability. The extent of permeability was determined by measuring the fluorescence of the receiver plate well solution over time. The cells were exposed to concentrations of TNF-α ranging from 25 to 200 ng/mL or varying exposure times to TNF-α in either ACCS or control media. The results for a 60 minute time course and 4 different concentrations of TNF-α are set forth in Table 1 below and the results for cumulative fluorescence experiment are set forth in Table 2 below.

TABLE 1

| | 60 minutes | |
|---|---|---|
| TNFα | ACCS (fluorescence) | Control Media (fluorescence) |
| 200 ng/ml | 335 | 505 |
| 100 ng/ml | 283 | 434 |
| 50 ng/ml | 248 | 503 |
| 25 ng/mL | 304 | 410 |

TABLE 2

| Time | ACCS + 50 ng/ml TNFα (fluorescence) | Control Media + 50 ng/mL TNFα (fluorescence) |
|---|---|---|
| 30 min | 168 | 482 |
| 60 min | 416 | 985 |
| 180 min | 1192 | 1580 |
| 360 min | 1638 | 2303 |

Results: After 60 minutes of exposure to TNF-α, the ACCS groups reduced permeability of the endothelial cells at all concentrations of TNF-α that were tested. The cumulative fluorescence demonstrated that, in the presence of ACCS, the endothelial cells were always less permeable that in cells treated with control media.

Example 2: Evaluate Whether ACCS can Modulate Increased Vascular Permeability as a Result of Irradiation Objective: Radiation is known to increase vascular permeability. Therefore, a second set of experiments was conducted to determine whether ACCS could modulate increased vascular permeability as a result of irradiation from a 5 Gy cesium-137 source.

Method: HUVECs were exposed to a radiation dose of 5 Gy prior to treatment with ACCS, control media, or endothelial growth media control.

Results: As shown in Table 3 below, ACCS Lot A-treated cells showed reduced FITC-Dextran fluorescence compared to endothelial growth media control, and control media. These results demonstrate that ACCS is modulating and therefore reducing vascular permeability. Table 4 shows that radiation exposure to the cells induced an increase in vascular permeability which was decreased by ACCS Lot A and Lot B compared to endothelial growth media control, and control media.

TABLE 3

| | Endothelial Growth Media Control (fluorescence) | ACCS (fluorescence) | Control media (fluorescence) |
|---|---|---|---|
| 5 Gy | 797 | 281 | 470 |

TABLE 4

| ACCS Lot A + 5Gy | ACCS Lot A | ACCS Lot B + 5Gy | ACCS Lot B | Control Media + 5Gy | Control Media | Endothelial Growth Medium Control + 5Gy | Endothelial Growth Medium Control |
|---|---|---|---|---|---|---|---|
| 13.3% | 8% | 11.8% | 5% | 21.1% | 13% | 17.0% | 11% |

Example 3: The Effect of ACCS on Reduction of Vascular Permeability in a Setting Wherein Radiation is Combined with TNF-α

Objective: Increased vascular permeability due to radiation may result from many stimuli in vivo. Radiation combined with inflammatory molecules may better simulate multiple inflammatory causes of permeability in vivo. To further evaluate the effect of ACCS on reduction of vascular permeability, HUVECs were exposed to both radiation and TNF-α, in various media.

Method: HUVECs were exposed to 5 Gy radiation and 50 ng/ml TNF-α for 4 hours.

Results: Both ACCS Lot A and Lot B showed reduced permeability of endothelial cells that were exposed to both 5 Gy radiation and 50 ng/mL TNF-α as compared to endothelial growth media control and control media.

TABLE 5

| | ACCS Lot A (fluorescence) | ACCS Lot B (fluorescence) | Endothelial Growth Media Control (fluorescence) | Control Media (fluorescence) |
|---|---|---|---|---|
| 5 Gy + 50 ng/ml TNF-α | 8.4 | 9.3 | 25.9 | 21.8 |

Example 4: ACCS Modulates Vascular Permeability In Vivo as Tested in the Miles Assay Objective: The purpose of this study was to evaluate whether or not ACCS can modulate vascular permeability in vivo using the Miles Assay (A. A. Miles AND E. M. Miles, Vascular reactions to histamine, histamine-liberator and leukotaxine in the skin of guinea-pigs, J. Physiol. (1952) 118, 228-257).

Method: Evans Blue Dye (5%) was administered intravenously to male rats weighing approximately 300 grams. The Evans Blue dye binds albumin present in the animal's blood stream. Test groups with and without vascular permeability stimulants were then injected intradermally on the flank of the animal forming a small bleb. Changes in vascular permeability were measured by quantifying the amount of Evans Blue dye present in a skin biopsy taken from each bleb site. After dye was extracted from the skin biopsies, the sample absorbance at 630 nm (the Evans Blue peak wavelength) was normalized to the initial biopsy weight in grams. The vascular permeability stimulants tested in this manner included histamine, TNF-α, VEGF and bradykinin. Doses of stimulant were chosen based on literature references.

Results: Table 6 below shows that compared to saline, ACCS reduced the Evans Blue signal induced by all stimulants tested. The reduction of Evans Blue is directly correlated with a reduction in vascular permeability at the injection site. Reduction in vascular permeability across all stimulants suggested that ACCS could be effective in multiple indications involving vascular permeability.

TABLE 6

Evans Blue dye Extraction ($ABS_{630}$/g tissue biopsy)

| 20 μg/mL Histamine | | 2 μg/mL TNF-α | | 4 μg/mL VEGF | | 20 μg/mL Bradykinin | |
|---|---|---|---|---|---|---|---|
| Saline | ACCS | Saline | ACCS | Saline | ACCS | Saline | ACCS |
| 1.330 | 0.291 | 0.505 | 0.203 | 1.449 | 0.519 | 1.28 | 0.71 |

Example 5: Effect of ACCS in an Animal Model of Viral Hemorrhagic Fever

ACCS is tested in animal models of viral hemorrhagic fever (see Badole, S. L. et al., Animal models for some important RNA viruses of public health concern in SEARO countries: Viral hemorrhagic fever, J Vector Borne Dis 52, March 2015, pp. 1-10; Qui, X., et al., Establishment and Characterization of a Lethal Mouse Model for the Angola Strain of Marburg Virus, November 2014. Volume 88, Number 21, Journal of Virology p. 12703-12714).

The present invention may be embodied in other specific forms without departing from the spirit or essential attributes thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference in its entirety into this specification.

What is claimed is:

1. A method of treating increased vascular permeability caused by a non-infectious disease, comprising administering to a patient in need thereof a therapeutically effective amount of amnion-derived cellular cytokine solution (ACCS), wherein the ACCS comprises physiological concentrations of vascular endothelial growth factor (VEGF), transforming growth factor beta (TGFβ), angiogenin, platelet-derived growth factor (PDGF), tissue inhibitor of metalloproteinase 1 (TIMP 1), and tissue inhibitor of metalloproteinase 2 (TIMP 2), and wherein the physiological concentrations range is ~5-16 ng/mL for VEGF, ~2.5-2.7 ng/ml for TGFβ2, ~3.5-4.5 ng/ml for angiogenin, ~100-165 pg/mL for PDGF, ~0.68 μg/mL for TIMP-1 and ~1.04 μg/mL for TIMP-2.

2. The method of claim 1, wherein the increased vascular permeability occurs in systemic inflammatory response syndrome (SIRS).

3. The method of claim 1, wherein the ACCS is administered parenterally.

4. The method of claim 3, wherein the parenteral administration is intravenous or intraperitoneal.

5. The method of claim 1, wherein the non-infectious disease is graft-versus-host disease (GVHD).

6. The method of claim 1, wherein the non-infectious disease is acute respiratory distress syndrome (ARDS).

7. The method of claim 1, wherein the ACCS reduces vascular permeability in endothelial cells.

* * * * *